US012805726B2

(12) United States Patent
Easson et al.

(10) Patent No.: US 12,805,726 B2
(45) Date of Patent: Nov. 24, 2026

(54) OPTICAL DIAGNOSTIC SENSOR SYSTEMS AND METHODS

(71) Applicant: Maxim Integrated Products, Inc., San Jose, CA (US)

(72) Inventors: Craig Alexander Easson, San Jose, CA (US); Joy T. Jones, San Jose, CA (US); John Hanks, Austin, TX (US); Khanh Q. Tran, Milpitas, CA (US); Arkadii V. Samoilov, Saratoga, CA (US)

(73) Assignee: Maxim Integrated Products, Inc., San Jose, CA (US)

( * ) Notice: Subject to any disclaimer, the term of this patent is extended or adjusted under 35 U.S.C. 154(b) by 1088 days.

(21) Appl. No.: 16/986,251

(22) Filed: Aug. 5, 2020

(65) Prior Publication Data

US 2021/0038080 A1 Feb. 11, 2021

Related U.S. Application Data

(60) Provisional application No. 62/885,081, filed on Aug. 9, 2019.

(51) Int. Cl.

*A61B 5/00* (2006.01)
*A61B 5/024* (2006.01)
(Continued)

(52) U.S. Cl.

CPC ........ *A61B 5/0059* (2013.01); *G02B 6/12004* (2013.01); *H10F 30/221* (2025.01);
(Continued)

(58) Field of Classification Search

CPC .............. A61B 5/0059; A61B 5/02416; A61B 5/02433; A61B 5/1455; A61B 5/14552;
(Continued)

(56) References Cited

U.S. PATENT DOCUMENTS 5,553,613 A * 9/1996 Parker .................. A61B 5/1455 600/347
9,618,635 B2 * 4/2017 Fechner .................. H10F 30/20
(Continued)

FOREIGN PATENT DOCUMENTS

CN 1638136 A1 7/2005
CN 103311256 A 9/2013
(Continued)

OTHER PUBLICATIONS

"Forrest, R. Filter-on-diode technology reaches maturity. Mar. 1, 1998. Detectors & Imaging. pp. 1-6" (Year: 1998).*
(Continued)

*Primary Examiner* — Severo Antonio P Lopez
(74) *Attorney, Agent, or Firm* — ArentFox Schiff LLP

(57) ABSTRACT

Described are embodiments of methods for determining physiological data, such as vital signs, by using an optical diagnostic sensor, the method comprising receiving at a semiconductor material, which is located between a photodiode and a trench, an opening into silicon, or a backside wafer-level package (WLP) coating, light of a first wavelength and light of a second wavelength that are above the wavelength of red light, the semiconductor material acting as a filter that blocks wavelengths below the wavelength of red light; detecting, at the photodiode, light of at least one of the first wavelength or the second wavelength; and using the detected light to determine a vital sign.

19 Claims, 8 Drawing Sheets

400

(51) Int. Cl.

| | |
|---|---|
| ***A61B 5/1455*** | (2006.01) |
| ***G02B 6/12*** | (2006.01) |
| ***H10F 30/221*** | (2025.01) |
| ***H10F 77/00*** | (2025.01) |
| ***H10F 77/122*** | (2025.01) |
| ***H10F 77/30*** | (2025.01) |
| ***H10F 77/40*** | (2025.01) |

(52) U.S. Cl.

CPC ......... *H10F 77/122* (2025.01); *H10F 77/306* (2025.01); *H10F 77/413* (2025.01); *H10F 77/933* (2025.01); *A61B 5/02416* (2013.01); *A61B 5/14552* (2013.01); *G02B 2006/12061* (2013.01); *G02B 2006/12102* (2013.01); *G02B 2006/12123* (2013.01); *G02B 2006/12138* (2013.01)

(58) Field of Classification Search

CPC ..... A61B 6/037; A61B 6/4241; A61B 5/0071; A61B 2562/0238; G02B 6/12002; G02B 6/12004; G02B 2006/12061; G02B 2006/12102; G02B 2006/12123; G02B 2006/12138; G01J 2003/2816; G01J 2001/446; H01L 31/02005; H01L 31/02161; H01L 31/02327; H01L 31/028; H01L 31/035281; H01L 31/10; H01L 31/103; H01L 27/14643; H01L 27/3227; G01T 1/248; G01T 1/2018

See application file for complete search history.

(56) References Cited

U.S. PATENT DOCUMENTS

2006/0071229 A1* 4/2006 Guenter ................ H01S 5/0261 257/E25.032
2011/0215432 A1* 9/2011 Uematsu ............ A61B 5/14552 257/E31.127
2011/0278436 A1* 11/2011 Rhodes ............. H01L 27/14629 977/755
2012/0120384 A1* 5/2012 Barrett ................. A61B 5/6866 356/41
2013/0242155 A1 9/2013 Oganesian
2014/0054461 A1 2/2014 Kalnitsky et al.
2015/0372185 A1* 12/2015 Rossi .................. H01L 31/1892 438/27
2016/0174843 A1 6/2016 Falconer et al.
2017/0337412 A1 11/2017 Bhat et al.
2017/0337413 A1 11/2017 Bhat et al.
2018/0116567 A1 5/2018 Ueda et al.

FOREIGN PATENT DOCUMENTS

CN 104425523 A1 3/2015
CN 106999114 A 8/2017
CN 107359174 A 11/2017
CN 109414225 A 3/2019

OTHER PUBLICATIONS

Promax, MAXM-2082P Validity Search Report, Optical Diagnostic Sensor Systems and Methods , dated Apr. 2020, (56 pgs).
Chinese office action mailed Dec. 27, 2023 in related Chinese patent application No. 202010794759.7
Response to Chinese office action filed Apr. 23, 2024 in related Chinese patent application No. 202010794759.7.
Chinese office action mailed Jul. 19, 2024 in related Chinese patent application No. 202010794759.7.
Response to Chinese office action filed Aug. 15, 2024 in related Chinese patent application No. 202010794759.7.
Chinese Office Action issued in Chinese Patent Application No. 202010794759.7 dated Feb. 6, 2025.
Chinese office action mailed Oct. 15, 2024 in related Chinese patent application No. 202010794759.7.
Response to Chinese office action filed Nov. 6, 2024 in related Chinese patent application No. 202010794759.7.

* cited by examiner

300

350

600

OPTICAL DIAGNOSTIC SENSOR SYSTEMS AND METHODS

CROSS-REFERENCE TO RELATED APPLICATIONS

This patent application is related to and claims priority benefit under 35 USC § 119 (e) to and commonly-owned U.S. Pat. App. No. 62/885,081 filed on Aug. 9, 2019, entitled “Optical Diagnostic Sensor Systems and Methods,” listing Craig Easson, Joy Jones, John Hanks, Khanh Tran, and Arkadii Samoilov as inventors, which patent document is incorporated by reference herein in its entirety and for all purposes.

BACKGROUND

A. Technical Field

The present disclosure generally relates to diagnostic sensors, such as vital sign monitors. More particularly, the present disclosure relates to systems and methods for optical diagnostic sensors.

B. Background

A pulse oximeter sensor is a noninvasive biometric optical sensor that utilizes optical IR signals reflected from blood vessels under the skin to measure peripheral oxygen saturation (SpO2) levels of a person’s blood. A pulse oximeter sensor may also be used as a photoplethysmography sensor that monitors periodically changing blood volume pulsations or perfusion in the skin. Detected optical IR signals may further be used to determine a person’s heart rate.

Today’s pulse oximetry is based on the red (wavelengths<700 nm) and infrared light (wavelengths>700 nm) absorption characteristics of oxygenated hemoglobin (HbO2) and deoxygenated or reduced hemoglobin (Hb) (see FIG. 1, chart 100). HbO2 absorbs more infrared light than Hb, i.e., HbO2 allows more red light to pass through than Hb. Conversely, Hb absorbs more red light and allows more infrared light to pass through. Since the ratio of the red light to the infrared light absorbed by the skin represents the ratio of HbO2 to Hb, the red/IR ratio can be converted to derive a SpO2 value, typically, by using a formula that has been empirically obtained.

While heart rate can be relatively simply derived from detected infrared light signals, a measurement of oxygenation (percentage of bound hemoglobin in the blood) commonly involves alternately shining infrared light and red light at an existing pulse oximetry sensor. The infrared light and red light are generated by two LEDs light sources that operate at two different wavelengths, for example, one LED that generates red light at a wavelength of about 660 nm and another LED that generates IR light at a wavelength of about 940 nm. The two wavelengths reflected from the skin are then measured, one at a time, by a photodiode within the sensor. The gathered information may then be used to calculate heart rate and determine the concentration of oxygen in the user’s blood vessels under the skin. Additionally, if the ratio of the AC component for the red light (i.e., the envelope of the heart rate pulse wave) to the DC component for red light divided by the ratio of the AC to DC components of IR light is measured, a (peripheral) perfusion index may be obtained.

BRIEF DESCRIPTION OF THE DRAWINGS

References will be made to embodiments of the invention, examples of which may be illustrated in the accompanying figures. These figures are intended to be illustrative, not limiting. Although the invention is generally described in the context of these embodiments, it should be understood that it is not intended to limit the scope of the invention to these particular embodiments. Items in the figures are not to scale.

Figure (“FIG.”) 1 shows different isosbestic points of oxygenated hemoglobin and deoxygenated hemoglobin in a range of 200 nm-1000 nm.

DETAILED DESCRIPTION OF EMBODIMENTS

Figure 1:
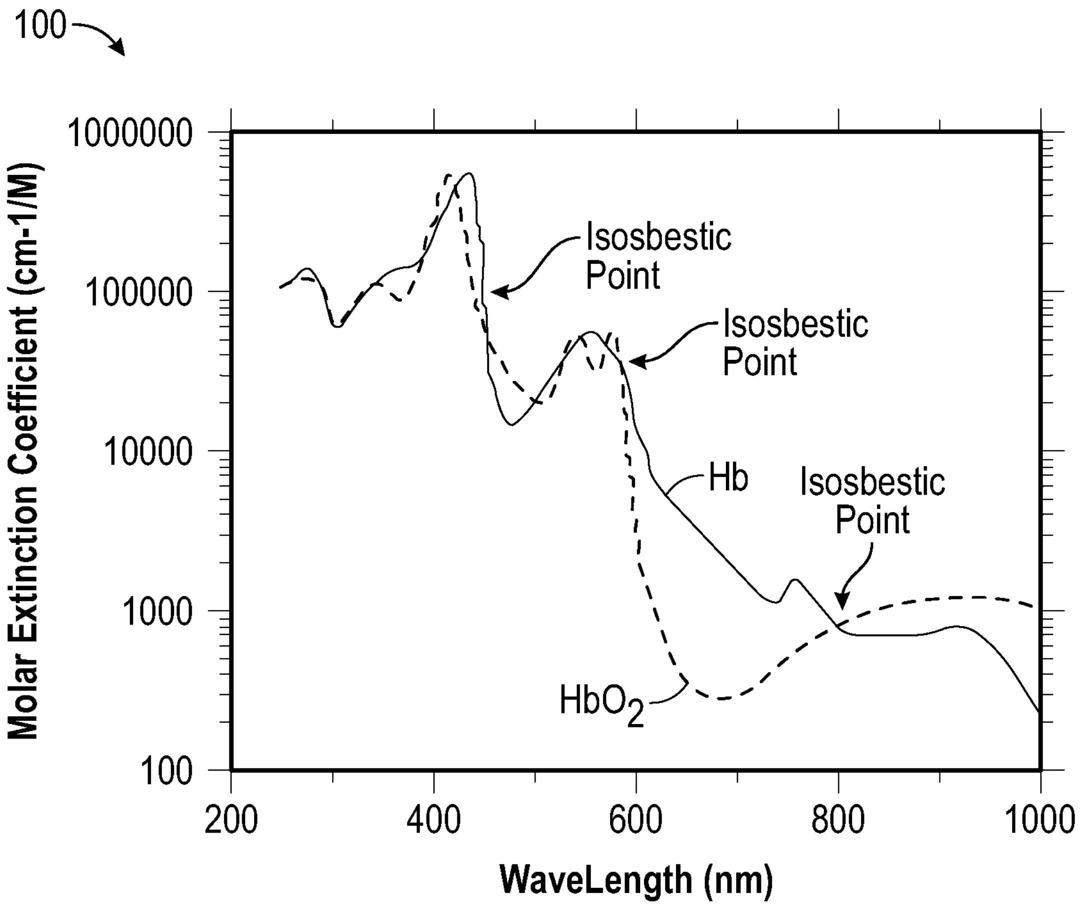

In the following description, for purposes of explanation, specific details are set forth in order to provide an understanding of the invention. It will be apparent, however, to one skilled in the art that the invention can be practiced without these details. Furthermore, one skilled in the art will recognize that embodiments of the present invention, described below, may be implemented in a variety of ways, such as a process, an apparatus, a system, a device, or a method on a tangible computer-readable medium.

Components, or modules, shown in diagrams are illustrative of exemplary embodiments of the invention and are meant to avoid obscuring the invention. It shall also be understood that throughout this discussion that components may be described as separate functional units, which may comprise sub-units, but those skilled in the art will recognize that various components, or portions thereof, may be divided into separate components or may be integrated together, including integrated within a single system or component. It should be noted that functions or operations discussed herein may be implemented as components. Components may be implemented in software, hardware, or a combination thereof.

Furthermore, connections between components or systems within the figures are not intended to be limited to direct connections. Rather, data between these components may be modified, re-formatted, or otherwise changed by intermediary components. Also, additional or fewer connections may be used. It shall also be noted that the terms “coupled,” “connected,” or “communicatively coupled” shall be understood to include direct connections, indirect connections through one or more intermediary devices, and wireless connections.

Reference in the specification to “one embodiment,” “preferred embodiment,” “an embodiment,” or “embodiments" means that a particular feature, structure, characteristic, or function described in connection with the embodiment is included in at least one embodiment of the invention and may be in more than one embodiment. Also, the appearances of the above-noted phrases in various places in the specification are not necessarily all referring to the same embodiment or embodiments.

The use of certain terms in various places in the specification is for illustration and should not be construed as limiting. A service, function, or resource is not limited to a single service, function, or resource; usage of these terms may refer to a grouping of related services, functions, or resources, which may be distributed or aggregated.

In this document photodiode and photodetector are used interchangeably. The terms "include," "including," "comprise," and "comprising" shall be understood to be open terms and any lists the follow are examples and not meant to be limited to the listed items.

Furthermore, one skilled in the art shall recognize that: (1) certain steps may optionally be performed; (2) steps may not be limited to the specific order set forth herein; (3) certain steps may be performed in different orders; and (4) certain steps may be done concurrently.

Furthermore, it shall be noted that embodiments described herein are given in the context of LEDs as light emitting devices, but one skilled in the art shall recognize that the teachings of the present disclosure are not limited to LEDs as other light emitting sources may equally be used.

Figure 2:
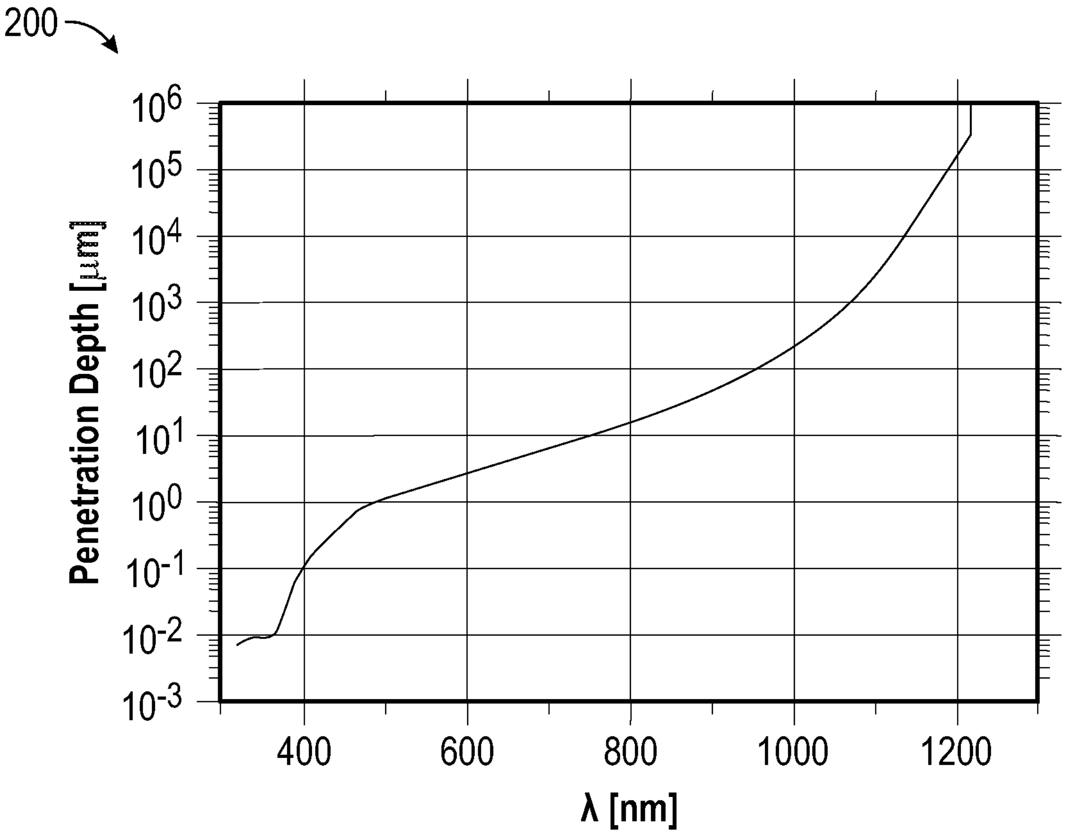
FIG. 2 shows the penetration depths of light of different wavelengths into a silicon material.

For infrared light applications, such as optical heart rate measurements, back-side-illumination (BSI) techniques deliver significant cost savings over front-side-illumination (FSI) methods. However, there are no known equivalent BSI applications for pulse oximetry sensors that measure SpO2. This is primarily due to the fact that the red light that SpO2 measurements require is absorbed within a relatively small penetration depth in the silicon substrate of the semiconductor device. As shown in chart 200 in FIG. 2, the silicon penetration depth for red light at a wavelength of about 660 nm is about 5 μm. This renders the use of existing BSI techniques for SpO2 measurements using a pulse oximetry sensor unfeasible.

Further, for certain sensors in consumer products, such as ear buds and hearing aids, observable red light that glows or blinks as the photodiode turns on and off is less than desirable. Furthermore, ear buds that rest against a person's skin require a relatively small footprint, e.g., they must have a small enough form factor to comfortable fit into a 4 mm-5 mm diameter ear canal.

Accordingly, what is need are systems and methods that can take advantage of cost and footprint reductions that BSI techniques offers, while, at the same time, avoiding aesthetically objectionable features in consumer products using optical diagnostic sensors such as pulse oximetry sensors.

Figure 3A:
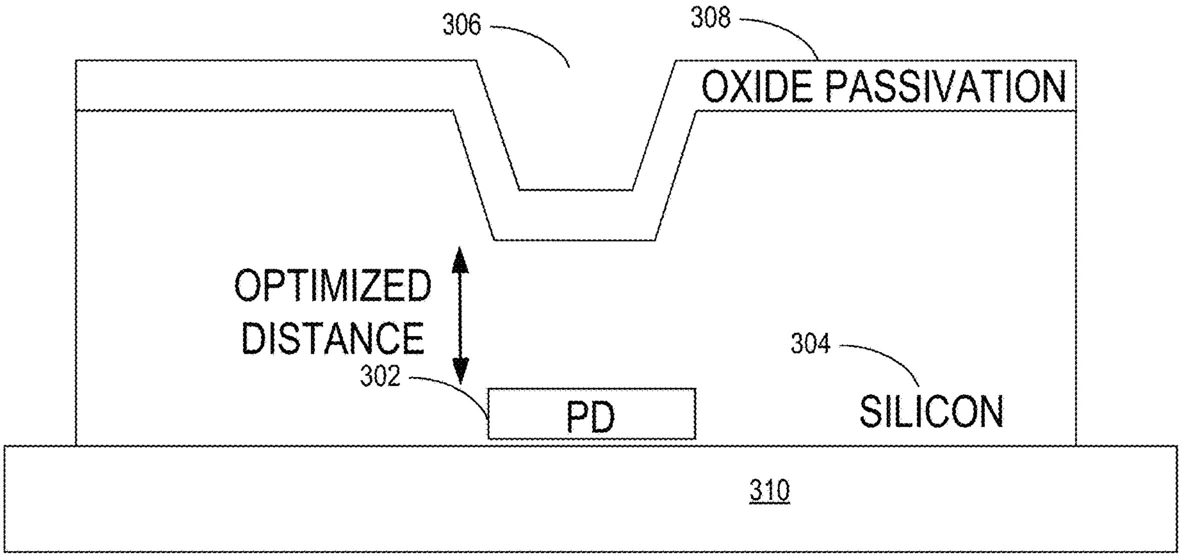
FIG. 3A illustrates a cross sectional view of a BSI chip that comprises a silicon substrate between a photodiode and a trench that is coated with an oxide passivation layer according to various embodiments of the present disclosure.
Figure 3B:
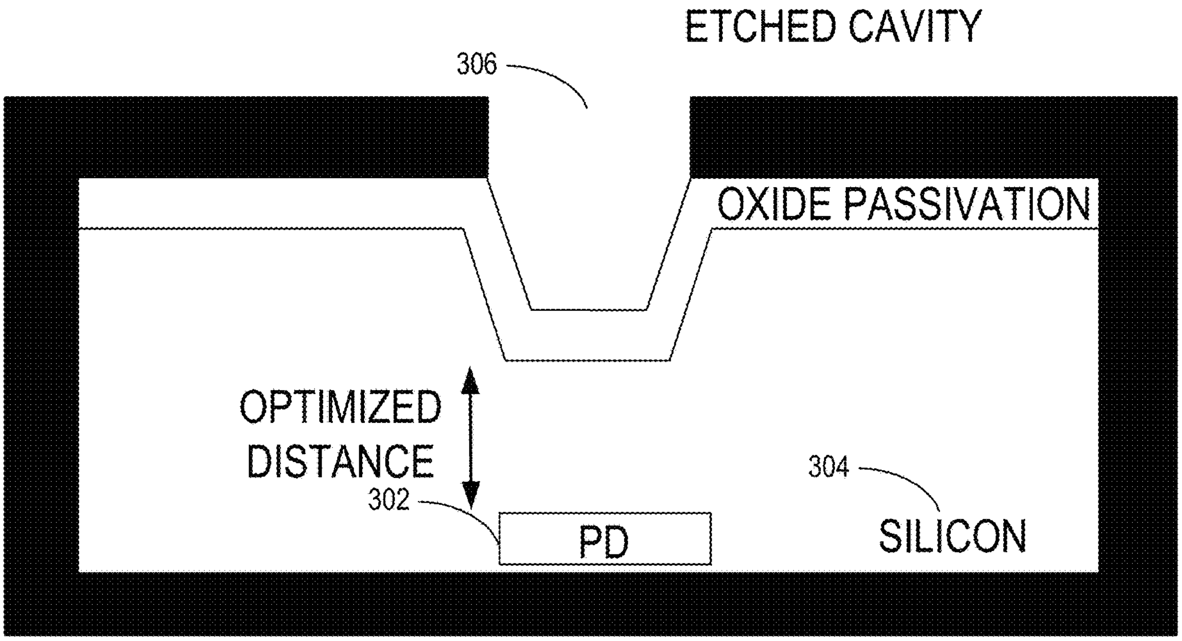
FIG. 3B illustrates a cross sectional view of BSI chip in FIG. 2 that comprises a cavity according to various embodiments of the present disclosure.

FIG. 3A illustrates a cross sectional view of a BSI chip that comprises a silicon substrate between a photodiode and a trench that is coated with an oxide passivation layer according to various embodiments of the present disclosure. FIG. 3B illustrates a cross sectional view of BSI chip in FIG. 2 that comprises a cavity according to various embodiments of the present disclosure. Chip 300 may be disposed on PCB 310 and, in embodiments, comprises photodiode 302, silicon substrate 304, and trench 306. As depicted in FIG. 3A, trench 306 may have sloped sidewalls and comprise oxide passivation layer 308. Photodiode 302 may be part of a photodetector (not shown).

In embodiments, the thickness of substrate 304 in region 330, i.e., between trench 306 and photodiode 302, may be chosen according to various optical properties of region 330. As mentioned in the background section above, the relatively low silicon penetration depth of red light renders BSI techniques impractical for SpO2 measurements by a pulse oximetry sensor that detects red LED light and an IR LED light.

Therefore, in embodiments of the present disclosure, instead of using one red LED and one IR LED, two light emitting sources (not shown in in FIG. 3A) may be used that both are capable of generating wavelengths outside of the visible spectrum (less than 700 nm) and closer to IR light (i.e., above 700 nm, e.g., 780 nm).

For implementations in which substrate 304 comprises mainly silicon, the thickness of the silicon substrate 304 does, therefore, not prevent IR light incident on trench 306 from sufficiently penetrating substrate 304. As a result, unlike for red light, the light of the two IR LEDs can reach photodiode 302. As an added advantage, undesirable "glowing" red light in sensors for consumer devices such as ear buds can be avoided.

In embodiments, the thickness of substrate 304 in region 330 may be adjusted by utilizing a dry etch or wet etch process during semiconductor manufacturing. In embodiments, etching increases the depth of trench 306 and lowers the thickness of region 330 to a desired thickness that permits IR wavelengths to pass through region 330, thus, allowing photodiode 302 to receive sufficient IR light from an IR light source.

In embodiments, region 330 may be adjusted such as to serve as a natural filter that advantageously eliminates the need for additional and costly filtering to block visible, ambient light. In addition, due to the bandgap of Si being about 1.12 μm, mid-IR wavelengths (>1000 nm) may also be "rejected" since photodiode 302 does not respond to wavelengths above the bandgap of Si. In embodiments, the thickness of region 330 is chosen such that the silicon penetration depth of the IR wavelengths of the LED is about 30 μm-60 μm depending on silicon starting material.

In embodiments, the width of photodiode 302 may be such as relatively small to ensure a relatively flat passivation layer 308 above photodiode 302 and to prevent "breadloafing" at the corners that, otherwise, would negatively impact uniformity in the light path.

In embodiments, an aperture (not shown) may be used to control the path of the photons that incident on photodiode 302. The aperture, e.g., and integrated aperture, may comprise a material that absorbs or reflects light such that a controlled beam of light may be formed at a desired region. In addition, the sensor may comprise a lens (not shown) adjacent to the aperture to aid in collecting the light.

It is understood that certain parts of chip 300 may serve as a light-guide that, in embodiments, may be coated with reflective material to reduce optical transmission losses. It is further understood that, while BSI chip 300 may be optimized for receiving and measuring light from two light sources at IR wavelengths, this is not intended as a limitation on the scope of the present disclosure.

In embodiments, the wavelengths of the light sources may be chosen such as to enable measurements associated with different isosbestic points than those shown in FIG. 1. For example, to measure wavelengths associated with an isosbestic point that may be located at a wavelength greater than 1000 nm, e.g., to facilitate glucose measurements at wavelengths of up to 2.5 μm, implementation details of a detector may be adjusted accordingly. This may be accomplished, for example, by choosing a suitable substrate material to accommodate measuring wavelengths beyond 1000 nm and optimizing the thickness above photodetector 302 according to optical characteristics of the material to allow to certain wavelengths to pass while blocking others, thereby, acting as an optical bandpass filter. Again, thickness may be controlled by controlling the depth of trench 306.

Figure 4:
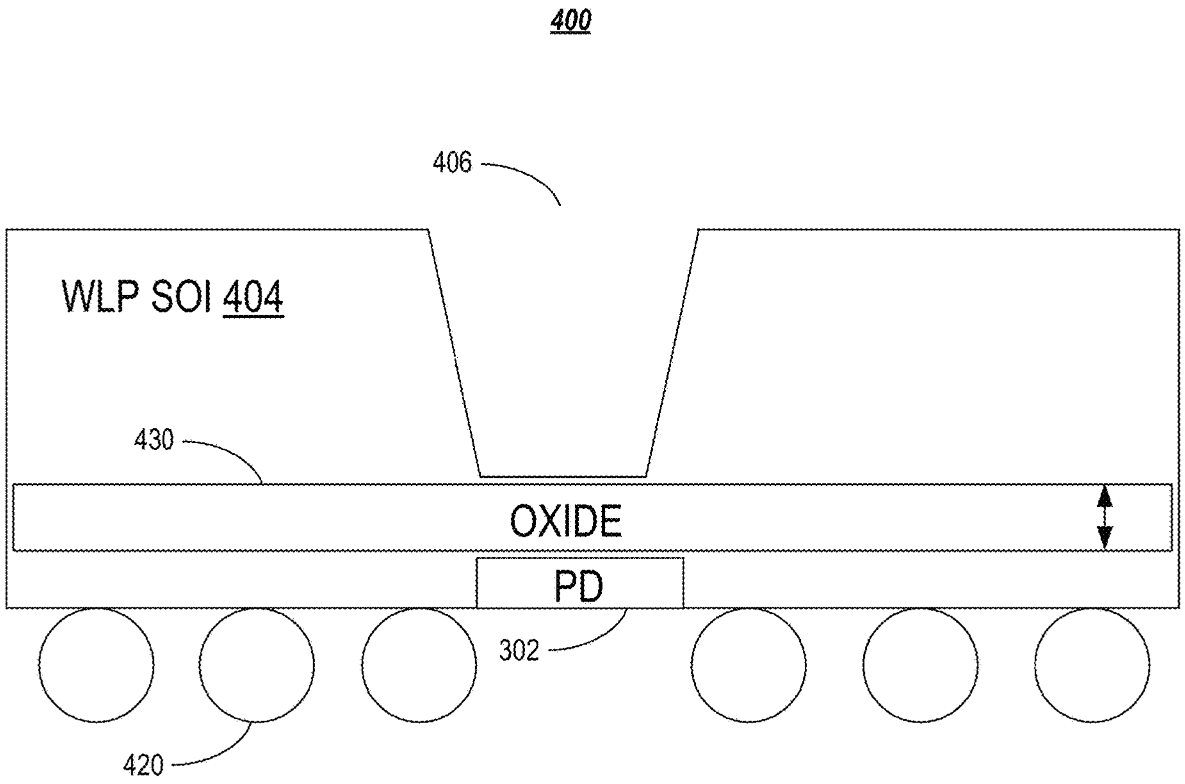
FIG. 4 illustrates a simplified cross sectional diagram of a BSI chip using a silicon-on-insulator (SOI) approach that comprises an oxide layer between a photodiode and a trench according to various embodiments of the present disclosure.

FIG. 4 illustrates a simplified cross sectional diagram of a BSI chip using an SOI approach that comprises an oxide layer between a photodiode and a trench according to various embodiments of the present disclosure. In a manner similar to FIG. 3A, in embodiments, chip 400 comprises photodiode 302, oxide layer 430, silicon substrate 404, bond balls 420, and trench 406. Bond balls 420, each having a certain diameter, may be disposed to the lower surface of substrate 410.

In embodiments, trench 406 may be etched to have sloped sidewalls to increase the number of photons collected by photodiode 302. The sidewalls may be coated, e.g., with reflective material to further increase the number of photons that reach photodiode 302. As depicted in FIG. 4, chip 400 may be a SOI structure with the insulator being formed by oxide 430. In embodiments, oxide 430 may serve as an etch stop that eliminates the need for coating trench 406 with a passivation layer.

In embodiments, optimizing the depth of trench 306, i.e., the thickness of the region above photodiode 302, advantageously eliminates the need for traditional packaging and allows the use of wafer-level packaging before dicing the wafer on which chip 400 is located, thus, providing substantial cost savings.

It is noted that the chips illustrated in FIG. 3A, FIG. 3B, and FIG. 4 are not limited to the constructional detail shown there or described in the accompanying texts. As those skilled in the art will appreciate, a suitable detector may be fabricated using different semiconductor manufacturing processing steps that may add or remove certain structures, e.g., layers, or parts thereof.

Figure 5:
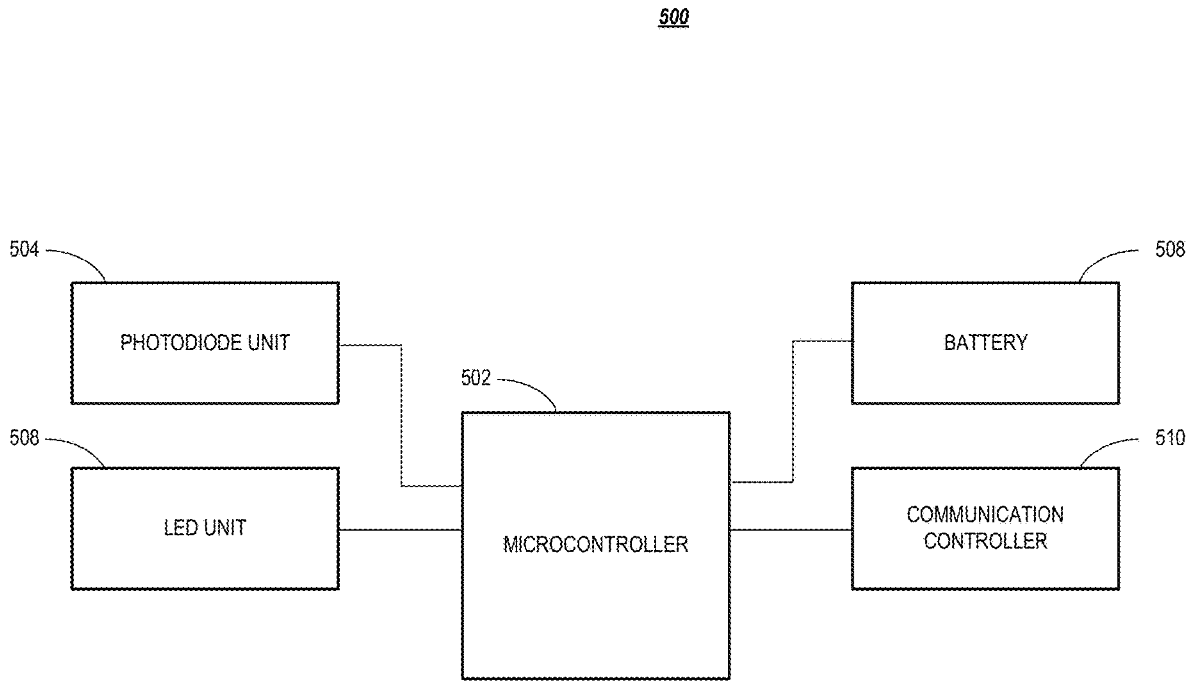
FIG. 5 is an exemplary block diagram illustrating an optical biometric sensor according to various embodiments of the present disclosure.

FIG. 5 is an exemplary block diagram illustrating an optical biometric sensor according to various embodiments of the present disclosure. Sensor 500 comprises microcontroller 502, photodiode unit 504, LED unit 506, battery 508, and communication controller 510. It is understood that LED unit may comprise one LED or an array of LEDs. Similarly, photodiode unit 504 may comprise one or more photodiodes. It is further understood that one or more components may be integrated on a single chip. As an example, LED unit 506, may be comprise one or more LEDs that are placed external to a chip comprising sensor 500. A person of ordinary skill in the art will appreciate that additional and different elements may be used to accomplish the objectives of the invention.

In embodiments, LED unit 508 may be placed adjacent to photodiode unit 504 that is capable of detecting incident IR light of one or more wavelengths. As mentioned with reference to FIG. 3A, by combining infrared signals or varying frequencies, photodiode unit 504 in biometric optical sensor 500 may be used to determine oxygen saturation levels of a user (e.g., a patient) using two IR wavelengths that are generated by LED unit 508. In addition, photodiode unit 504 may also be configured to determine heart rate from an infrared light signal generated by LED unit 508. As such sensor 500 may be employed as a multi-functional biometric sensor.

When measuring heart rate or O2 saturation levels, e.g., after an initialization process, sensor 500 may collect user data, e.g., by using a combination of two different lights in the infrared spectrum. In embodiments, the light may be alternatively produced by two infrared LED light sources that project light of two wavelengths into the user's skin. Upon the light signals being reflected from the user's skin, they may be detected using photodiode 504. The gathered data; especially, the ratio of the two light signals or components thereof, may then be used to calculate the concentration of oxygen in the user's blood vessels under the skin surface, determine a heart rate, and the like. This approach advantageously eliminates the need for a transmissive measurement through the person's finger, which involves placing a wired clip around the finger.

In embodiments, microcontroller 502 within sensor 500 digitizes the signals from light sensor or LED unit 508 to calculate the heart rate/oxygen saturation levels before outputting the result, which may be further processed, as desired.

One of skill in the art will appreciate that additional electronics, such as noise filtering elements, etc., may be implemented to support the functions of sensor 500 according to the objectives of the invention. For example, an actively controlled boost regulator may be implemented to improve the noise performance of sensor 500.

Figure 6:
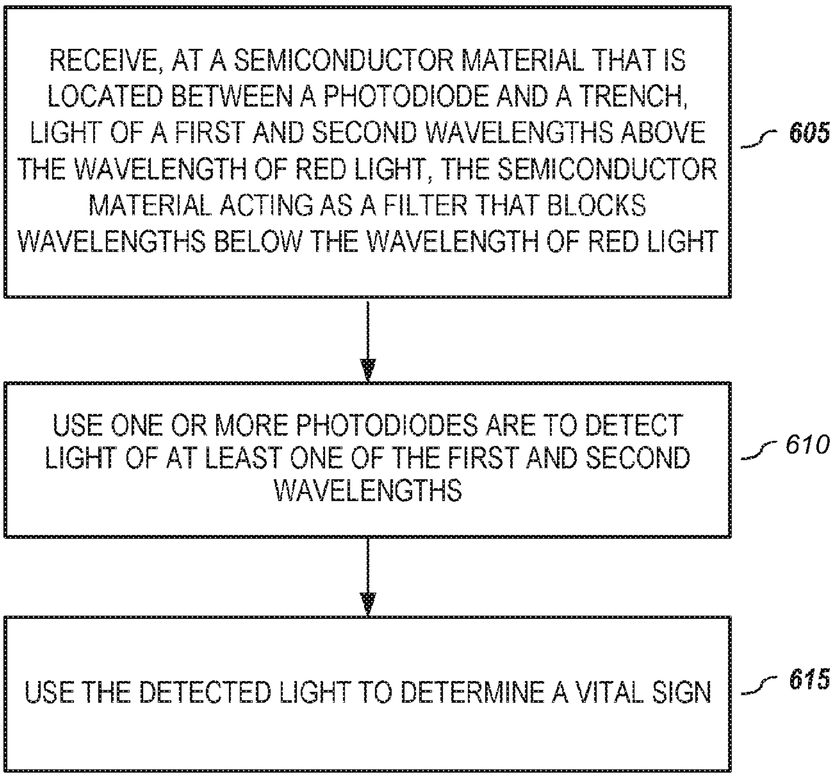
FIG. 6 is a flowchart of an illustrative process of determining a vital sign according to various embodiments of the present disclosure.

FIG. 6 is a flowchart of an illustrative process of determining a vital sign according to various embodiments of the present disclosure. In embodiments, process 600 determining a vital sign adjusting starts at step 605 when light of a first and second wavelengths above the wavelength of red light are received at a semiconductor material that is located between a photodiode and a trench. The semiconductor material, e.g., a substrate material (silicon or poly-silicon) or an oxide material that may serve as an etch stop layer, due to its chosen thickness is optimized to act as a filter that blocks wavelengths below the wavelength of red light.

The first and second wavelengths may be generated by one or more internal or external LEDs that generate light, e.g., in the near-IR range from 700 μm-1000 μm.

At step 610, one or more photodiodes are used to detect light of at least one of the first and second wavelengths. It is understood that one photodiode may be used to measure light of one of two LEDs at a time, e.g., by toggling to alternately measure light from two LEDs.

Finally, at step 615, the detected light is used to determine a vital sign.

Figure 7:
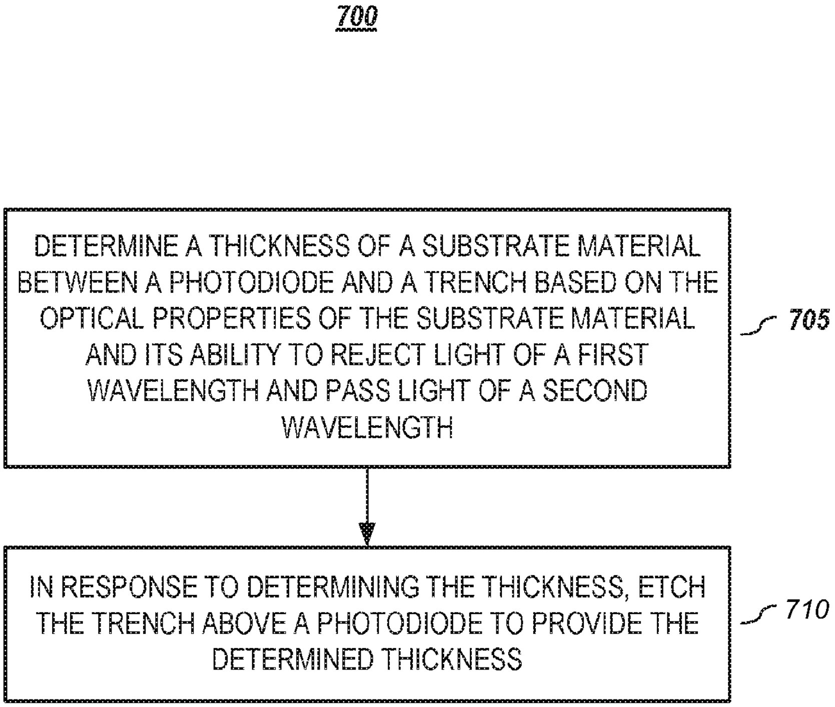
FIG. 7 is a flowchart of an illustrative process for manufacturing an optical sensor that for detecting a vital according to various embodiments of the present disclosure.

FIG. 7 is a flowchart of an illustrative process for manufacturing an optical sensor that for detecting a vital according to various embodiments of the present disclosure. In embodiments, manufacturing process 700 starts at step 705 by determining a thickness of a substrate material between a photodiode and a trench. In embodiments, the determination is based on the optical properties of the substrate material and its ability to reject light of a first wavelength and pass light of a second wavelength.

At step 710, in response to determining the thickness, the trench above a photodiode is etched to provide the determined thickness.

Aspects of the present invention may be encoded upon one or more non-transitory computer-readable media with instructions for one or more processors or processing units to cause steps to be performed. It shall be noted that the one or more non-transitory computer-readable media shall include volatile and non-volatile memory. It shall be noted that alternative implementations are possible, including a hardware implementation or a software/hardware implementation. Hardware-implemented functions may be realized using ASIC(s), programmable arrays, digital signal processing circuitry, or the like. Accordingly, the "means" terms in any claims are intended to cover both software and hardware implementations. Similarly, the term "computer-readable medium or media" as used herein includes software and/or hardware having a program of instructions embodied thereon, or a combination thereof. With these implementation alternatives in mind, it is to be understood that the figures and accompanying description provide the functional information one skilled in the art would require to write program code (i.e., software) and/or to fabricate circuits (i.e., hardware) to perform the processing required.

It shall be noted that embodiments of the present invention may further relate to computer products with a non-transitory, tangible computer-readable medium that have computer code thereon for performing various computer-implemented operations. The media and computer code may be those specially designed and constructed for the purposes of the present invention, or they may be of the kind known or available to those having skill in the relevant arts. Examples of tangible computer-readable media include, but are not limited to: magnetic media such as hard disks, floppy disks, and magnetic tape; optical media such as CD-ROMs and holographic devices; magneto-optical media; and hardware devices that are specially configured to store or to store and execute program code, such as application specific integrated circuits (ASICs), programmable logic devices (PLDs), flash memory devices, and ROM and RAM devices. Examples of computer code include machine code, such as produced by a compiler, and files containing higher level code that are executed by a computer using an interpreter. Embodiments of the present invention may be implemented in whole or in part as machine-executable instructions that may be in program modules that are executed by a processing device. Examples of program modules include libraries, programs, routines, objects, components, and data structures. In distributed computing environments, program modules may be physically located in settings that are local, remote, or both.

One skilled in the art will recognize no computing system or programming language is critical to the practice of the present invention. One skilled in the art will also recognize that a number of the elements described above may be physically and/or functionally separated into sub-modules or combined together.

It will be appreciated to those skilled in the art that the preceding examples and embodiments are exemplary and not limiting to the scope of the present disclosure. It is intended that all permutations, enhancements, equivalents, combinations, and improvements thereto that are apparent to those skilled in the art upon a reading of the specification and a study of the drawings are included within the true spirit and scope of the present disclosure. It shall also be noted that elements of any claims may be arranged differently including having multiple dependencies, configurations, and combinations.

What is claimed is:

1. A method for determining physiological data using an optical diagnostic sensor, the method comprising:

receiving at a semiconductor material light of a first wavelength and light of a second wavelength, wherein both the first wavelength and the second wavelength are in a near-infrared range;

wherein the semiconductor material is a silicon-on-insulator silicon substrate with a front-side photodiode and a backside trench aligned to the photodiode, the trench having a floor, and wherein an oxide layer between the photodiode and the trench serves as an etch stop that defines a remaining silicon thickness between the floor and the photodiode, the remaining silicon thickness substantially blocking visible light while transmitting near-infrared light to the photodiode;

detecting, at the photodiode, light at at least one of the first wavelength and the second wavelength received through the remaining silicon thickness; and using the detected light to determine physiological data.

2. The method according to claim 1, wherein both the first wavelength and the second wavelength are in a near-infrared (near-IR) range from 700 nm to 1000 nm inclusive.

3. The method according to claim 1, wherein the light of the first wavelength and the light of the second wavelength are associated with an isosbestic point that is located at a wavelength greater than a near-infrared (near-IR) wavelength.

4. The method according to claim 1, wherein the trench comprises sidewalls that are sloped to increase photon collection.

5. The method according to claim 1, wherein the trench is coated with reflective material and comprises a region that serves as a waveguide.

6. The method according to claim 5, wherein solder balls are disposed on a substrate outside of the region and adjacent to the photodiode.

7. The method according to claim 1, wherein the remaining silicon thickness is in a range of 30 μm to 80 μm inclusive.

8. An optical biometric sensor system for determining physiological data, the optical biometric sensor system comprising:

a power source configured to energize the sensor system;

light sources configured to generate light of a first wavelength and light of a second wavelength that are in a near-infrared range;

a silicon substrate having a front side and a backside, the silicon substrate comprising a silicon-on-insulator structure;

a photodiode formed in the front side and configured to detect light having the first wavelength and light having the second wavelength;

a trench formed in the backside and aligned with the photodiode, the trench having a floor;

a remaining silicon thickness between the photodiode and the trench, wherein the remaining silicon thickness is configured to substantially block visible light while transmitting light in the near-infrared range to the photodiode;

an oxide layer between the photodiode and the trench serving as an etch stop to define the remaining silicon thickness; and a microcontroller coupled to the light sources and the photodiode, wherein the microcontroller is configured to digitize a signal from the photodiode to determine physiological data.

9. The optical biometric sensor system according to claim 8, wherein the first wavelength and the second wavelength are associated with an isosbestic point that is located at a wavelength greater than a near-infrared (near-IR) wavelength.

10. The optical biometric sensor system according to claim 8, further comprising an aperture and a lens that increases an amount of the light detected at the photodiode, the lens being integrated with the aperture.

11. The optical biometric sensor system according to claim 8, wherein the trench is coated with reflective material, the trench comprising a region that serves as a waveguide.

12. The optical biometric sensor system according to claim 11, further comprising solder balls disposed on a substrate outside of the region and adjacent to the photodiode.

13. The optical biometric sensor system according to claim 8, wherein the light sources are further configured to project the generated light of the first wavelength and the light of the second wavelength into skin of a user and the microcontroller uses a ratio of the light having the first wavelength and light having the second wavelength or components thereof as detected by the photodiode to determine the physiological data.

14. A biometric sensor comprising:

a silicon substrate having a front side and a backside, the silicon substrate comprising a silicon-on-insulator structure;

a photodiode formed at the front side of the silicon substrate;

a trench formed from the backside of the silicon substrate and aligned with the photodiode, the trench having a floor;

a remaining silicon thickness between the floor of the trench and the photodiode, the remaining silicon thickness being configured to substantially block visible light while transmitting near-infrared light; and an oxide layer between the photodiode and the trench serving as an etch stop to define the remaining silicon thickness, wherein the biometric sensor is configured to receive light of a first wavelength and light of a second wavelength, both the first wavelength and the second wavelength being in a near-infrared range, through the remaining silicon thickness to the photodiode.

15. The biometric sensor of claim 14, wherein the sensor comprises no light source disposed in the trench or on the silicon substrate, and the light of the first wavelength and the light of the second wavelength are generated by light-emitting diodes external to the sensor.

16. The biometric sensor of claim 14, wherein sidewalls of the trench are sloped and comprise a reflective coating to increase photon collection toward the photodiode.

17. The biometric sensor of claim 14, further comprising an oxide passivation layer disposed on the trench.

18. The biometric sensor of claim 14, wherein the remaining silicon thickness cooperates with a responsivity cutoff of the photodiode to reject wavelengths above approximately 1000 nm.

19. The biometric sensor of claim 14, wherein the photodiode is configured to detect alternately the light of the first wavelength and the light of the second wavelength received through the remaining silicon thickness to support determination of physiological data.

* * * * *